United States Patent [19]

Castel

[11] Patent Number: 4,587,957
[45] Date of Patent: May 13, 1986

[54] TISSUE AND BONE REGENERATION

[75] Inventor: John C. Castel, Lake Forest, Ill.

[73] Assignee: Physio Technology, Inc., Topeka, Kans.

[21] Appl. No.: 422,306

[22] Filed: Sep. 23, 1982

Related U.S. Application Data

[63] Continuation-in-part of Ser. No. 294,714, Aug. 20, 1981.

[51] Int. Cl.$^4$ ............................................. A61N 1/42
[52] U.S. Cl. ...................................... 128/1.3; 128/1.5
[58] Field of Search ................................ 128/1.3–1.5, 128/653, 804

[56] References Cited

FOREIGN PATENT DOCUMENTS

| 716954 | 12/1931 | France | 128/1.5 |
| 1665 | of 1872 | United Kingdom | 128/1.3 |
| 342419 | 2/1931 | United Kingdom | 128/804 |

OTHER PUBLICATIONS

Nogi, "Magnetic Flux Source for Medical and Biological Use", WO 8001648, Published Aug. 1980–face sheet only.
Benthall, R. H., "Inductors for HF Electromagnetic Therapy Apparatus", GB 2027594 (U.K. Pat. Appln.) publ. Feb. 1980.

Primary Examiner—Kyle L. Howell
Assistant Examiner—Francis J. Jaworski
Attorney, Agent, or Firm—Wood, Dalton, Phillips, Mason & Rowe

[57] ABSTRACT

An apparatus and technique is disclosed for promoting or altering the growth, repair or regenerative process of living tissues and cells with an induced magnetic field. The apparatus includes at least one coil of a specific structural arrangement coupled to a current generator for producing a magnetic field and mounted on a flexible contour-conforming composition for application to living tissue. The generator provides current to the coil to produce a continuous or pulsating magnetic field within the region to be treated. A "polaroid" filter formed also of a flexible contour is disposed between the coil and the region to be treated to control flux density. Additional filter(s) can be placed adjacent each other to further control the orientation and density of the flux impinging upon the area to be treated. The number of filters and their arrangement are selected to provide beneficial effects in the area of the tissue to be treated.

10 Claims, 7 Drawing Figures

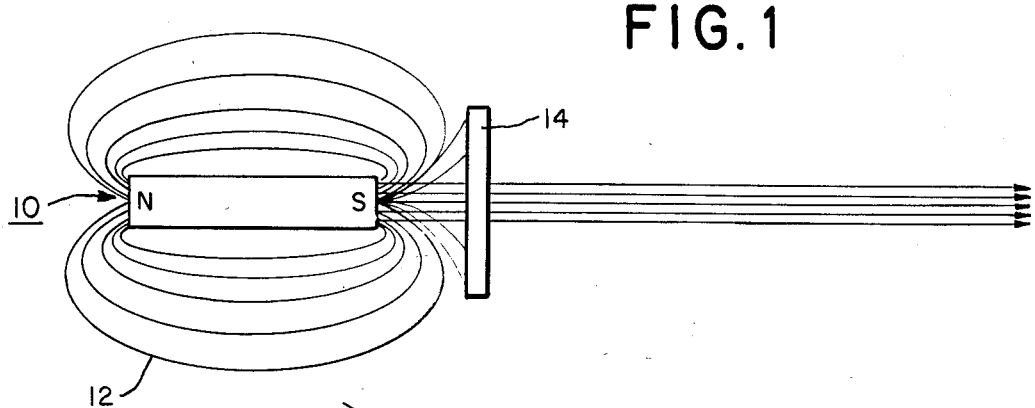
FIG. 1
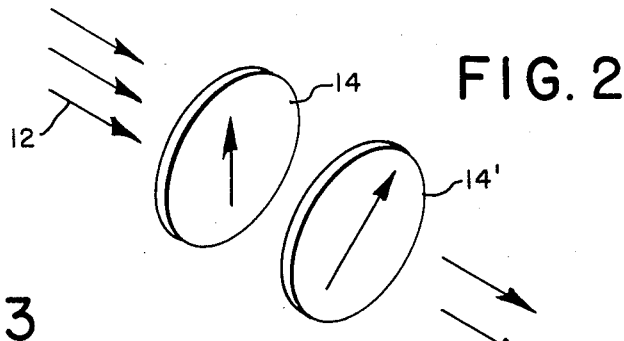
FIG. 2
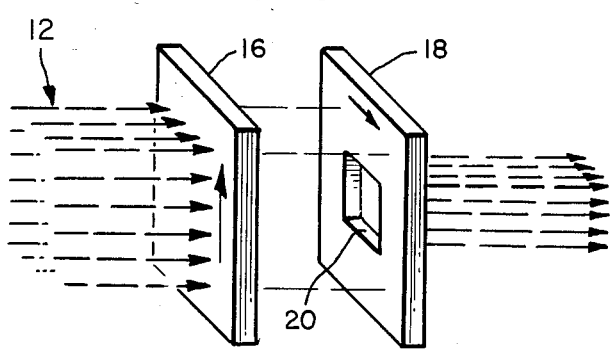
FIG. 3
FIG. 4
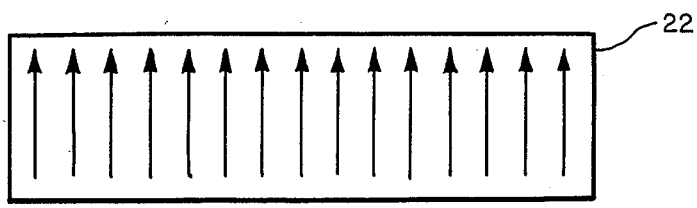
FIG. 5
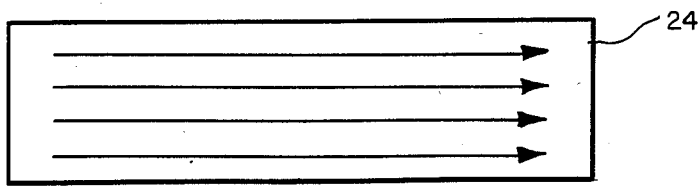

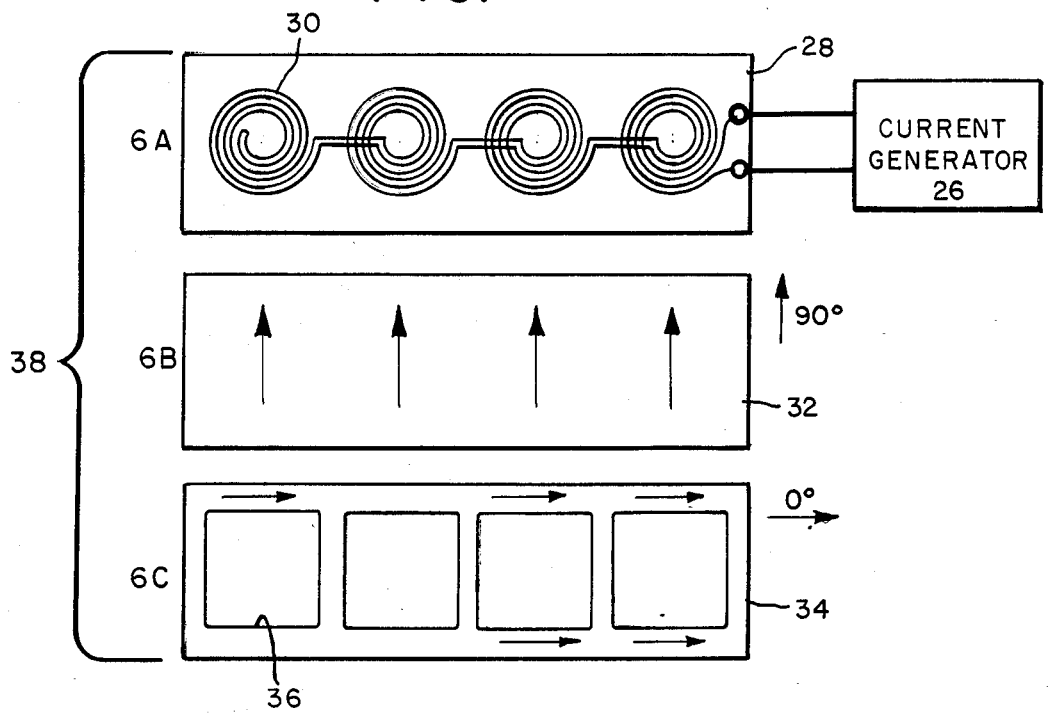
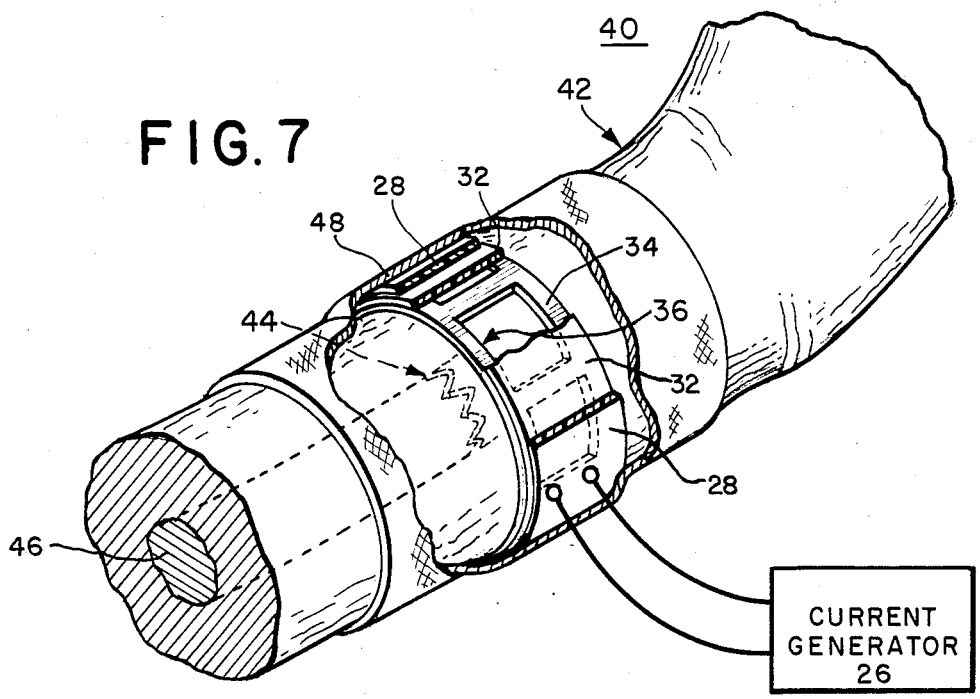

TISSUE AND BONE REGENERATION

RELATED APPLICATIONS

This application is a continuation-in-part of application Ser. No. 294,714 filed Aug. 20, 1981 entitled "Electromagnetic Coil for Tissue Treatment" by John C. Castel. The material disclosed in that application is specifically incorporated herein by reference.

BACKGROUND

The present invention relates to electromagnetic apparatus for treating living tissue and more particularly to the control of magnetic fields for the treatment of the living tissue.

As discussed in the above identified copending application, I have developed a structure and technique capable of providing electromagnetic energy for tissue treatment sufficiently versatile to accommodate localized application of a magnetic field for therapeutic purposes.

A current generator coupled to a conductive pattern(s) is attached to or implanted within a flexible substrate adapted to conform to the tissue to be treated. The pattern provides a magnetic field when current is applied to the pattern. When adjacent the tissue to be treated, the magnetic field provides therapeutic effects.

I recognize that the device described above and the therapeutic effects resulting therefrom, and capable of providing electromagnetic energy to tissue treatment in localized areas and under a variety of conditions and uses. However, improved results may be obtained by the additional control of the direction and density of the magnetic flux applied to the tissue to be treated. The present invention has therefore been developed to overcome the shortcomings of the known techniques and devices of the prior art, generally, and, more specifically, to improve upon the device outlined in my co-pending application.

SUMMARY OF THE INVENTION

The present invention includes a current generator coupled to at least one conductive pattern formed for providing treatment of cells or tissue. The conductive pattern is attached to or implanted within a flexible insulating substrate which will conform to the contour of the tissue to be treated. When current is provided to the conductive pattern, a magnetic field is produced in the pattern. A single "polarizing" filter or a plurality of such filters also of a flexible contour is disposed between the conductive pattern and the tissue to be treated to control the magnetic flux density which provides beneficial therapeutic effects to the tissue. A single filter so disposed provides for the control of the vector position of the magnetic flux of the field with respect to the area to be treated. This is particularly helpful in promoting more rapid healing in the repair of bone fractures. The deployment of two or more filters disposed between the conductive pattern and the tissue to be treated provides for varying the intensity of the flux density applied to the tissue. Additionally, two or more filters adjacent each other and disposed between the pattern and the tissue to be treated may provide apertures through which a magnetic flux of a defined orientation may pass. The impingement of a collimated field upon the tissue to be treated may have therapeutic effects in the regeneration of tissue, the repair of bone, and general tissue repair.

It is therefore a feature of the invention to provide a magnetic treating device which is simple and inexpensive for treating living tissue.

It is another feature of the invention to provide a structure for producing a magnetic field with improved coupling characteristics for tissue treatment.

It is still another feature of the invention to provide a structure for producing a magnetic field for tissue treatment which easily conforms to the area to be treated.

Still another feature of the invention is to control the position and orientation of a magnetic field by the use of "POLAROID" filters.

Yet another feature of the present invention is to employ "POLAROID" filters to promote healing and tissue repair.

It is a further feature of the invention to selectively apply a magnetic field of a defined density to a selected point to be treated while at the same time excluding the remainder of the magnetic field from adjacent areas.

These and other novel features of the present invention will become apparent from the following detailed description of the invention when taken with the accompanying drawings wherein:

BRIEF DESCRIPTION OF THE DRAWING

FIG. 1 is an illustrative diagram of a magnet and a flux density "POLAROID" filter employed in accordance with the present invention;

FIG. 2 is a perspective view of two "POLAROID" filters with different flux density vector orientation;

FIG. 3 is a perspective view of two "POLAROID" filters employed for selectively excluding the passage of the magnetic field;

FIG. 4 and FIG. 5 depict flexible "POLAROID" filters for films having different flux density orientation;

FIG. 6A is a schematic diagram of a coil as the conductive patterned on a flexible insulating material for generating the magnetic field in accordance with the present invention;

FIG. 6B depicts a flexible flux density "POLAROID" fiter having a vector orientation of ninety degrees;

FIG. 6C depicts a flexible flux density "POLAROID" filter with apertures therein having a vector orientation of zero degrees; and FIG. 7 is a perspective view of an embodiment of an apparatus for treating tissue in accordance with the present invention.

DETAILED DESCRIPTION OF PREFERRED EMBODIMENTS

Referring to FIG. 1, a magnet 10 has a north pole N and a south pole S with flux density lines 12 extending from one pole to the other in a typical well-known manner. Although the magnet 10 is shown to be of the bar magnet type, any kind of magnet may be employed to practice the present invention so long as it is capable of forming flux density lines 12. Disposed within the magnetic field is a "POLAROID" filter 14 employed in accordance with the present invention. The filter 14 is an old device more commonly known in optics and having the property of passing light of a single polarity. The material is manufactured by Polaroid, Inc. and is available in flexible or rigid sheets through Edmund Scientific, Co. Although any particular sheet thickness is suitable, I have found 0.03" thick flexible material having a transmissibility factor of 23% to 25% is preferred. It should be noted that the "POLAROID" filter 14 selectively excludes a portion of the magnetic field depending upon the vector orientation of the filter, as shall be described below.

Referring to FIG. 2, flux density lines 12 are shown in a perspective manner traversing "POLAROID" filter 14, and then "POLAROID" filter 14' has a vector orientation of approximately ninety degrees, whereas "POLAROID" filter 14' has a vector orientation angle of approximately thirty degrees. It is apparent that the angle between the vector orientation of one filter is opposed to the other determines the amount of flux density ultimately passing through both filters 14 and 14', as is true when light traverses the filters. For example, if the vector orientation of the first filter is exactly ninety degrees with respect to the second filter, only an incidental amount of flux will traverse both filters (as is the analogous condition for light). Similarly, if the defined angle between the two flux patterns is zero, flux density traverses both filters as if they were one. As the angle between the filters increases toward ninety degrees, the flux density traversing both filters decreases.

Referring to FIG. 3 and offered in an effort to explain the principle employed in the present invention, flux density 12 is shown to impinge upon two adjacent "POLAROID" filters 16 and 18. The filter 16 has a flux vector orientation of ninety degrees, whereas the flux vector orientation of filter 18 is zero degrees. Additionally, flux density filter 18 has an aperture 20. Flux 12 passing through filter 16 is inhibited by filter 18 except for that flux which passes through aperture 20. It is apparent that by the appropriate selection of the filters directive flux impingement upon the area to be treated is easily realized.

Referring to FIG. 4 and FIG. 5, individual flexible "POLAROID" filters, each 0.03" thick and capable of forming to a selected contour, are shown. It is apparent from the arrows on the individual filters 22 and 24 that the vector orientation, when compared to each other, is approximately ninety degrees as shown. Filters 22 and 24 may be placed in a stacked relationship, and suitably secured to each other so that one single unit is provided, yet are still sufficiently flexible to form a contour. One skilled in the art will realize that a defined angle between the two filters of less than ninety degrees may provide for the selection of a controlled amount of flux density passing through both filters when one is adjacent to the other. When the filters are placed in stacked relationship to each other and a magnetic field is placed alongside, the flux density passing through both filters depends upon the defined angle between the vector orientation of the filters or whether an aperture has been created in either one or both filters. Flux is significantly restricted from passing through the filters if the angular relationship between their respective orientation is ninety degrees.

Turning now to FIGS. 6A, 6B and 6C, one embodiment of the device in accordance with the present invention is shown. The device includes a current generator 26 capable of producing a continuous or low frequency pulsating unipolar or bipolar current, as more fully described in my copending application. Typically, the generator may be operated at a frequency from ten to one hundred Hertz as described in the copending application. The output of the generator 26 is coupled to a magnetic field producing structure which includes a mounting substrate 28 and a plurality of conductive pattern 30. Mounting substrate 28 may be constructed of a variety of well-known materials but preferably as a cloth or flexible plastic or electrical insulating material and having a planar configuration and thickness and flexibility which allows it to conform to the contours of the surface upon which it is placed. The conductive pattern 30 is formed in any conventional manner but preferably as a fine wire attached to or embedded in the substrate 28. Deposited upon substrate 28 and in side by side or juxtaposed relationship is flexible "POLAROID" filter 32 having the vector orientation noted by the arrow in the top right corner. The material is flexible and has a thickness of 0.03" which allows it to conform to the contours established by the substrate 28. As noted in FIG. 6C, deposited in juxtaposed or adjacent relationship to the "POLAROID" filter 32 is yet a second flux density "POLAROID" filter 34 having a polarity ninety degrees displaced from the polarity of the first filter. This filter has a configuration, thickness and flexibility which allows it to conform to the contours of the surface upon which it is applied as well. Filter 34 is provided with an aperture(s) 36 such that flux generated by conductive pattern(s) 30 passes through both filters in a manner identical to the passing of flux shown in FIG. 3.

The device shown in FIG. 7 contemplates the sandwich structure 38 formed by the substrates shown in 6A through 6C and is shown to wrap or surround the anatomy 40 to be treated, as for example the break in the bone as shown. As shown, anatomy 40 typifies on extremity 42 having a fracture 44 of bone 46. Sandwich structure 38 is wrapped about the anatomy 40 at the fracture 44 so that the magnetic flux provided by generator 28 (via conductive pattern(s) 30) and controlled by the selection of filter 32 and/or filter 34 impinges upon fracture 44 for therapeutic healing. A cast (not shown) may be applied to the extremity 42 as well.

The controlled impingement of flux, in accordance with the present invention, has improved therapeutic healing effects when compared to the indiscriminate application of a magnetic field known to the prior art.

Magneticlly permeable material 48 in flexible form may be wrapped about the substrate above or below a cast to increase the magnetic flux intensity which ultimately impinges upon the selected portion of the tissue to be repaired. Alternatively, iron filings may be deposited in a plaster cast which will also increase the permeability.

I claim:

1. An apparatus for treating tissue comprising:
    means for producing a magnetic field to be directed an area, a portion of which is defined by the surface of tissue to be treated; and
    blocking means comprising a pair of facially juxtaposed polarizing filter sheets, one of said sheets having a flux-passing aperture therein, said sheets being arranged at a preselected angle of polarization relative to each other to block transmission of the flux through overlapping areas thereof, thereby to controlledly pass through said aperture only magnetic flux from said means for producing the magnetic field and arranged to be facially abutted to an area including said surface of the tissue to be treated.

2. The apparatus if claim 1 further including means superimposed upon said means for producing a magnetic field for enhancing the intensity of the magnetic field.

3. The apparatus of claim 2 wherein said means for enhancing the intensity of the magnetic field include a flexible permeable material.

4. The apparatus of claim 2 wherein said means for enhancing the intensity of the magnetic field comprises iron particles.

5. An apparatus for treating tissue comprising:
means for producing a plurality of side-by-side magnetic fields to impinge on a preselected area, a portion of which is defined by the surface of tissue to be treated; and
blocking means comprising a pair of facially juxtaposed polarizing filter sheets, one of said sheets having a flux-passing aperture therein, said sheets being arranged at a preselected angle of polarization relative to each other to block transmission of the flux through overlapping areas thereof, said blocking means being arranged to be removably disposed between said means for producing the magnetic fields and said tissue to be treated for polarizing the flux impinging upon different portions of the surface of said tissue to be treated and blocking flux from impinging on portions intended to not receive flux, thereby controlledly applying polarizing magnetic radiation only to preselected portions of said area defining said surface.

6. The apparatus of claim 5 wherein one filter sheet is fixedly juxtaposed to the other filter sheet.

7. The apparatus of claim 5 wherein said polarizing filter sheets comprise flexible "POLAROID" material.

8. The apparatus of claim 5 further including means superimposed upon said means for producing a magnetic field for enhancing the intensity of the magnetic field.

9. The apparatus of claim 8 wherein said means for enhancing the intensity of the magnetic field include a flexible permeable material.

10. The apparatus of claim 8 wherein said means for enhancing the intensity of the magnetic field comprises iron particles.

* * * * *